United States Patent [19]

Faust

[11] Patent Number: 4,511,555

[45] Date of Patent: Apr. 16, 1985

[54] HERBAL HAIR TREATMENT COMPOSITIONS

[76] Inventor: Valerie F. Faust, 4009 Glenwood Rd., Brooklyn, N.Y. 11210

[21] Appl. No.: 424,279

[22] Filed: Sep. 27, 1982

[51] Int. Cl.³ .................... A61K 7/06; A61K 35/78; C07G 17/00
[52] U.S. Cl. .................................. 424/74; 424/195.1
[58] Field of Search ............... 424/195, 74; 260/236.5

[56] References Cited

U.S. PATENT DOCUMENTS

| 896,647 | 8/1908 | Mackay | 424/74 |
|---|---|---|---|
| 3,732,111 | 6/1971 | Berner et al. | 260/236.5 |

FOREIGN PATENT DOCUMENTS

| 104265 | 3/1917 | United Kingdom | 424/74 |

OTHER PUBLICATIONS

W. Lewis, Medical Botany, pp. 338, 339, Wiley & Sons, New York 1977.
M. Keller, Mysterious Herbs & Roots, pp. 310, 295, Peace Press 1978.

*Primary Examiner*—Albert T. Meyers
*Assistant Examiner*—John W. Rollins, Jr.
*Attorney, Agent, or Firm*—Florence U. Reynolds

[57] ABSTRACT

The compositions in the form of pomades, shampoos or conditioners contain a cosmetically acceptable carrier and an effective amount for controlling dandruff of a vegetable oil extract of sage and/or Indian hemp, optionally combined with rosemary. The extract is obtained by heating the herbs either alone or in combination in a vegetable oil for about 3 to 5 hours at about 100° to 190° F. followed by filtering off residual solids.

5 Claims, No Drawings

HERBAL HAIR TREATMENT COMPOSITIONS

BACKGROUND OF THE INVENTION

This invention relates to herbal hair treatment compositions which are effective in controlling dandruff.

Various herbal hair treatment products are on the market, such as pomades, aqueous rinses, shampoos, and conditioners.

The present invention relates to such products containing an oily herbal extract which is especially effective in controlling dandruff.

SUMMARY OF THE INVENTION

The invention relates to hair treatment compositions comprising a vegetable oil extract of one or more of the following herbs: Indian hemp leaves (Pilocorpus selloanus), sage stems and leaves (Salvia officinalis) and rosemary needles (Rosmarinus officinalis). The extract is prepared by heating the finely divided herbs, either separately or in combination, in a vegatable oil at a temperature of about 100° to 190° F. for about 3 to 5 hours. The extract may then be incorporated into conventional formulations used in manufacturing hair pomades, shampoos and conditioners. Regular, frequent use, preferably daily, over a period of 2 to 6 weeks results in a substantial elimination of dandruff.

DETAILED DESCRIPTION

Preparation of Extract

One or more of the following herbs, Indian hemp leaves, sage stems and leaves and rosemary needles, in their natural state, either fresh or dry, are ground in a food processor for about 2 minutes. The finely divided material is then heated in a vegetable oil for about 3 to 5 hours, preferably 4 hours, at a temperature of about from 100° to 190° F., preferably 110° F., with stirring every hour or more often at the higher temperatures, until the oil attains a green color. The mixture is cooled, then filtered or strained to remove undissolved solids.

A preferred ratio of herbs to oil is 24 oz. by wt. of each herb in 176 fluid oz. of oil. This yields 96 fluid oz. of extract when heated for 4 hours at 110° F. Up to 2 gallons of oil per 72 oz. by wt. of herbs may be used but this just produces a weaker extract and has no special advantage.

The vegetable oil may consist of one or more oils such as semi-drying oils, e.g., corn oil, soybean oil and cottonseed oil; drying oils, e.g., sunflower oil and safflower oil; and non-drying oils, e.g., peanut oil and olive oil. The preferred oils are corn oil, soybean oil and cottonseed oil because they are the least expensive.

The use of aluminum pans and utensils should be avoided since aluminum seems to react with the herbs.

Preparation of a Pomade

In order to prepare a pomade from the above extract, the 96 fluid oz. of extract, as prepared above, are blended into 24 lbs. of pure white petroleum jelly (petrolatum). Then 2 cups of pure olive oil and 1 oz. of an oil-soluble fragrance such as Indian musk, are added in any order and thoroughly mixed to form a homogeneous finished product. The amount of olive oil may vary slightly depending upon the consistency desired.

A more concentrated and hence faster acting pomade may be prepared by using a ratio of 128 fluid oz. of extract to 24 lbs. of petroleum jelly.

The pomade is used in the following way for normal and dry hair: part the hair and place a little of the pomade on the finger and apply to the scalp until the entire scalp has been greased. Then massage in gently and style the hair. The pomade should be used daily for best results but should be used at least once a week. For people with oily hair, the pomade may be applied as above, allowed to remain on the scalp and hair overnight and shampooed out in the morning.

It was found that pomades containing ground herbs in a similar pomade base did not provide a product with the effective properties of controlling dandruff.

The following are examples of shampoo and conditioner formulations in which the oily herb extract according to the invention may be incorporated.

| Shampoo Formulation | |
|---|---|
| pbw | |
| 400 | monoethanolamine lauryl sulfate |
| 50 | ethylene glycol monostearate |
| 450 | water |
| 80 | lecithin |
| 20 | oil extract of herbs |
| 1,000 | |

| Conditioner Formulation | |
|---|---|
| pbw | |
| 50 | stearyl dimethylbenzyl ammonium chloride |
| 20 | ethylene glycol monostearate |
| 30 | cetyl alcohol |
| 800 | water |
| 80 | lecithin |
| 20 | oil extract of herbs |
| 1,000 | |

The above products are applied daily or several times a week in the conventional manner for best results.

The invention has been described with reference to specific embodiments which are merely illustrative and not intended to limit the scope of the invention as defined in the claims.

I claim:

1. An herbal hair treatment composition for controlling dandruff comprising a cosmetically acceptable carrier and a vegetable oil extract of sage, Indian hemp, and rosemary prepared by heating 24 oz. by wt. each of sage stems and leaves, Indian hemp leaves, and rosemary needles in 176 to 256 fluid oz. of a vegetable oil for about 3 to 5 hours at a temperature of about 100° to 190° F. with agitation, followed by filtering off residual solids from the extract.

2. The hair treatment composition of claim 1 wherein said vegetable oil is selected from the group consisting of corn oil, soybean oil and cottonseed oil.

3. The hair treatment composition of any one of claims 1 and 2 in the form of a pomade.

4. The hair treatment composition of any one of claims 1 and 2 in the form of a shampoo.

5. The hair treatment composition of any one of claims 1 and 2 in the form of a conditioner.

* * * * *